United States Patent
Mullins et al.

(10) Patent No.: US 6,474,152 B1
(45) Date of Patent: Nov. 5, 2002

(54) METHODS AND APPARATUS FOR OPTICALLY MEASURING FLUID COMPRESSIBILITY DOWNHOLE

(75) Inventors: Oliver C. Mullins, Ridgefield, CT (US); Andrew Kurkjian, Sugar Land, TX (US); Robin McGowan, Garches (FR); Thomas Distefano, New Orleans, LA (US); Ian Traboulay, Sugar Land, TX (US)

(73) Assignee: Schlumberger Technology Corporation, Sugar,Land, TX (US)

( * ) Notice: Subject to any disclaimer, the term of this patent is extended or adjusted under 35 U.S.C. 154(b) by 36 days.

(21) Appl. No.: 09/704,630

(22) Filed: Nov. 2, 2000

(51) Int. Cl.[7] .................... E21B 47/00; E21B 49/10; G01N 7/00
(52) U.S. Cl. ................. 73/152.22; 73/152.27; 73/152.52; 73/152.18; 175/41; 175/50; 166/250.01; 250/255
(58) Field of Search ............... 73/152.22, 152.24, 73/152.27, 152.52; 166/250.01, 254.2, 250.07; 175/50, 48, 41, 40; 250/255, 256, 338.5

(56) References Cited

U.S. PATENT DOCUMENTS

| | | | |
|---|---|---|---|
| 2,550,844 A | 5/1951 | Meiller et al. ............... 48/190 |
| 2,966,055 A | 12/1960 | Tracht et al. ................ 73/170 |
| 3,780,575 A | 12/1973 | Urbanosky ................... 73/155 |
| 3,859,851 A | 1/1975 | Urbanosky ................... 73/155 |
| 4,833,915 A | * 5/1989 | Radd et al. ................... 73/153 |
| 4,860,581 A | 8/1989 | Zimmerman et al. ......... 73/155 |
| 4,936,139 A | 6/1990 | Zimmerman et al. ......... 73/155 |
| 4,994,671 A | 2/1991 | Safinya ...................... 250/255 |
| 5,167,149 A | 12/1992 | Mullins ....................... 73/155 |
| 5,201,220 A | 4/1993 | Mullins ....................... 73/155 |
| 5,226,310 A | * 7/1993 | Steiger ......................... 73/38 |
| 5,247,830 A | 9/1993 | Goode ......................... 73/155 |
| 5,266,800 A | 11/1993 | Mullins ...................... 250/256 |
| 5,329,811 A | * 7/1994 | Schultz et al. ............... 73/155 |
| 5,331,156 A | 7/1994 | Hines et al. ................. 250/256 |
| 5,473,939 A | * 12/1995 | Leder et al. .................... 73/155 |
| 5,635,631 A | * 6/1997 | Yesudas et al. ............. 73/61.46 |
| 5,708,204 A | * 1/1998 | Kasap ...................... 73/152.52 |
| 5,837,893 A | * 11/1998 | Chu ........................ 73/152.52 |
| 5,859,430 A | 1/1999 | Mullins et al. ............. 250/255 |
| 5,939,717 A | 8/1999 | Mullins ..................... 250/255 |
| 6,176,323 B1 | * 2/2001 | Weirich et al. ............... 175/40 |
| 6,189,612 B1 | * 2/2001 | Ward ..................... 166/250.19 |

OTHER PUBLICATIONS

White, J.E., Underground Sound Application of Seismic Waves, 1983, Dept. Geophysics, Colorado School of Mines, pp. 58–60.

Ostrander, W.J., Plane–Wave Reflection Coefficients fo rGas Sands at Nonnormal Angles of Incidence, Oct. 1984, 52nd Annaual International SEG, Geophysics vol. 49, No. 10, pp. 1637–1648.

Mullins, et al., Effect of High Pressure on the Optical Detection of Gas by Index–of–Refraction Methods, Dec. 1994, Applied Optics, vol. 33, No. 34, pp. 7963–7970.

Communication–13 European Patent Office Search Report Jan. 24, 2002.

* cited by examiner

*Primary Examiner*—Hezron Williams
*Assistant Examiner*—David J. Wiggins
(74) *Attorney, Agent, or Firm*—John Ryberg; J.L. Jennie Salazar

(57) ABSTRACT

The compressibility of a formation hydrocarbon sample is determined downhole by using a borehole tool to obtain the sample downhole, and, at two different pressures, subjecting the sample to near infrared illumination and conducting spectral absorption measurement of peaks at and/or around about 6,000 $cm^{-1}$ and/or at and/or about 5,800 $cm^{-1}$ (the absorption peaks of methane and crude oil respectively). The compressibility of the sample is determined from the change in the peak areas, the change in pressure, and the measured peak area itself. According to a preferred embodiment of the invention, the pressure is changed at least 2000 pounds per square inch (psi), and preferably 4000 or more psi between measurements.

21 Claims, 5 Drawing Sheets

METHODS AND APPARATUS FOR OPTICALLY MEASURING FLUID COMPRESSIBILITY DOWNHOLE

The present invention is related to co-owned U.S. Pat. No. 4,860,581 to Zimmerman et al., 4,936,139 to Zimmerman et al., 4,994,671 to Safinya et al., No. 5,167,149 to Mullins et al., 5,201,220 to Mullins et al., No. 5,247,830 to Goode, No. 5,266,800 to Mullins et al., and No. 5,331,156 to Hines et al., 5,859,430 to Mullins et al., and 5,939,717 to Mullins, all of which are hereby incorporated by reference herein in their entireties.

BACKGROUND OF THE INVENTION

1. Field of the Invention

The present invention relates to the analysis of downhole borehole fluids. More particularly, the present invention relates to apparatus and methods for the in situ determination of compressibility of hydrocarbon fluids in a geological formation.

2. State of the Art

Naturally occurring hydrocarbon fluids include a wide range of fluids including dry natural gas, wet gas, condensate, light oil, black oil, heavy oil, and heavy viscous tar. The physical properties of these various hydrocarbon fluids, such as density, viscosity, and compressibility vary considerably. In addition, the separation of each of the hydrocarbon fluid compositions into distinctly separate gas, liquid and solid phases, each with its own physical properties, occur at certain contours of pressure and temperature. This is referred to generally as the "phase behavior" of the hydrocarbon.

The economic value of a hydrocarbon reserve, the method of production, the efficiency of recovery, the design of production hardware systems, etc., all depend upon the physical properties and phase behavior of the reservoir hydrocarbon fluid. Hence, it is important that the fluid properties and phase behavior of the hydrocarbon be determined accurately following the discovery of the hydrocarbon reservoir, so that a decision of whether it is economically viable to develop the reservoir can be made; and if viable, an appropriate design and plan for the development of the reservoir can be adopted. With that in mind, those skilled in the art will appreciate that the ability to conduct an analysis of formation fluids downhole (in situ) is extremely desirable.

The assignee of this application has provided a commercially successful borehole tool, the MDT (a trademark of Schlumberger) which analyzes formation fluids in situ. The MDT extracts and analyzes a flow stream of fluid from a formation in a manner substantially as set forth in co-owned U.S. Pat. Nos. 3,859,851 and 3,780,575 to Urbanosky, as well as U.S. Pat. Nos. 4,860,581 and 4,936,139 to Zimmerman et al., which are hereby incorporated by reference herein in their entireties. The OFA (a trademark of Schlumberger), which is a module of the MDT, determines the identity of the fluids in the MDT flow stream and quantifies the oil and water content based on the previously incorporated related patents. In particular, previously incorporated U.S. Pat. No. 4,994,671 to Safinya et al. provides a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly in order to quantify the amount of water and oil in the fluid. As set forth in previously incorporated U.S. Pat. No. 5,266,800 to Mullins, by monitoring optical absorption spectrum of the fluid samples obtained over time, a determination can be made as to when a formation oil is being obtained as opposed to a mud filtrate. Thus, the formation oil can be properly analyzed and quantified by type. Further, as set forth in the previously incorporated U.S. Pat. No. 5,331,156 to Hines et al., by making optical density measurements of the fluid stream at certain predetermined energies, oil and water fractions of a two-phase fluid stream may be quantified.

The Safinya et al., Mullins, and Hines et al. patents represent great advances in downhole fluid analysis, and are particularly useful in the analysis of oils and water present in the formation. The issues of in situ gas quantification and analysis are addressed in the previously incorporated U.S. Pat. Nos. 5,167,149 to Mullins et al., 5,201,220 to Mullins et al., 5,859,430 to Mullins et al., 5,939,717 to Mullins, and in O.C. Mullins et al., "Effects of high pressure on the optical detection of gas by index-of-refraction methods", *Applied Optics*, Vol. 33, No. 34, pp. 7963–7970 (Dec. 1, 1994). In particular, U.S. Pat. No. 5,859,430 to Mullins et al. discloses a method and apparatus for the downhole compositional analysis of formation gases which utilizes a flow diverter and spectrographic analysis. More particularly, the apparatus includes diverter means for diverting formation gas into a separate stream, and a separate gas analysis module for analyzing the formation gas in that stream. The methods and apparatus of the '647 application are useful in determining what types of gas are present in the formation fluid. U.S. Pat. No. 5,939,717 to Mullins, on the other hand, is directed to methods and apparatus for determining in situ gas-oil ratios (GOR) which are necessary for establishing the size and type of production facilities required for processing newly discovered oil.

Despite the large advances set forth above made in the downhole analysis and quantification of oil, gas, and water, and gas-oil ratios, additional information regarding physical properties of the hydrocarbons such as the hydrocarbon compressibility are desired. A determination of hydrocarbon compressibility is desirable for at least two reasons. First, as a result of production, the pressure of the reservoir fluid will be reduced. The extent of this reservoir pressure reduction is a function of compressibility, as fluids of large compressibility will maintain their pressure with modest production, whereas very incompressible fluids will suffer a significant pressure drop with modest production. The reduction in pressure results in a reduction in the rate of production, and possibly undesired phase transitions. It is important to be able to predict in advance of production the expected pressure behavior of the reservoir, and therefore, one must know the fluid compressibility.

Second, the compressibility can also be used to help determine the volume of the reservoir. In particular, a 3D seismic technique is often used to image the subsurface structure, and identify the compartment sizes and shapes in the formation. Then an amplitude versus offset (AVO) technique such as described in W. J. Ostrander, Geophysics, 49,1637 (1984) may be used within the 3D seismic technique to identify variations in the compressibility of fluid which is saturating the subsurface formations. A direct determination of compressibility, therefore, may be used to re-process the seismic data, and in this way, obtain (in other words, "back out") an improved estimate of the size and shape of the hydrocarbon reservoir compartment.

Fluid compressibility is defined as the fractional change in volume that is associated with a change in pressure. Mathematically, compressibility β is defined according to:

$$\beta = \frac{-1}{V}\left(\frac{\partial V}{\partial P}\right)_T \quad (1)$$

where $\partial V$ is a change of volume, V is an initial volume, $\partial P$ is a change in pressure, and T is a constant and known temperature.

Various methods are presently known for determining the compressibility of formation fluids in situ. A sonic logging tool can measure the velocity of compressional and shear waves within the formation, and if the elastic properties of the rock matrix are known via other means, it may be possible to determine the compressibility of the saturating fluid from the measured velocities. See, for example, J. E. White, "Underground Sound", Elsevier Publishing Co., New York (1983). However, the compressibility measurement obtained in this manner is "dynamic" and does not always yield reliable results. Also, borehole fluid testing tools such as the previously described MDT tool can be used to measure fluid compressibility by using a pressure gauge in conjunction with a known volumetric compression capacity. However, precise measurements of small volumetric changes are extremely difficult to obtain; especially downhole. In addition, the measurement of an extrinsic property such as volume requires certainty that all fluid involved in the measurement is the desired fluid. Again, this is difficult to ensure downhole.

SUMMARY OF THE INVENTION

It is therefore an object of the present invention to provide methods and apparatus for making in situ determinations of the compressibility of hydrocarbon fluids.

It is another object of the invention to provide methods and apparatus for measuring hydrocarbon fluid compressibility without the necessity for measuring volumetric compression.

It is a further object of the invention to provide methods for measuring hydrocarbon fluid compressibility utilizing presently available borehole tools.

It is an additional object of the invention to measure in situ the compressibility of a hydrocarbon fluid by subjecting the fluid to direct measurement of other properties.

In accord with these objects which will be discussed in detail below, the methods and apparatus of the present invention arise from discoveries by the present inventors about the light absorption properties of hydrocarbons at certain near infrared (NIR) wavelengths. In particular, it was discovered that, for a given hydrocarbon fluid in a formation, the change in the optical absorption at certain wavelengths which results due to a change in pressure correlates directly with the compressibility of the hydrocarbon fluid. In other words, a change in pressure applied to the hydrocarbon fluid will result in a change in the amount of light absorbed by the fluid at certain wavelengths, and the relationship between the two is a direct indication of the compressibility of the fluid. In addition, it was discovered that for each different hydrocarbon, there is a different linear relationship between the mass density of that hydrocarbon and optical "peak area" for that hydrocarbon, where the peak area is defined as the integral of the absorption spectrum for that hydrocarbon around a certain absorption peak.

Therefore, methods according to the invention include providing an OFA-type tool which subjects formation fluids to NIR illumination and which provides a spectral absorption measurement of peaks at and/or around about 6,000 $cm^{-1}$ and/or at and/or about 5,800 $cm^{-1}$ (the absorption peaks of methane and crude oil respectively), measuring the spectral absorptions at two different pressures, and determining the compressibility from the change in the peak areas, the change in pressure, and the measured peak area itself. According to a preferred embodiment of the invention, the pressure is increased at least two thousand psi, and preferably 4000 or more psi between measurements.

According to the invention, a borehole apparatus is provided for measuring the hydrocarbon fluid compressibility includes a testing region, a conduit for directing formation fluid into the testing region, means for increasing pressure on the fluid in the testing region, means for measuring the pressure (or a change of pressure) on the fluid in the testing region, a light source emitting at least near infrared rays into the testing region, a spectral detector optically coupled to the testing region, and a processor coupled to the spectral detector. The testing region is a transparent tube or chamber which is located between the light source and the spectral detector such that light directed from the light source to the spectral detector is interrupted by formation fluid. The spectral detector is preferably a spectrometer which measures the spectrum of the light which has been transmitted through the formation fluid in the testing region. The processor is preferably a microprocessor.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
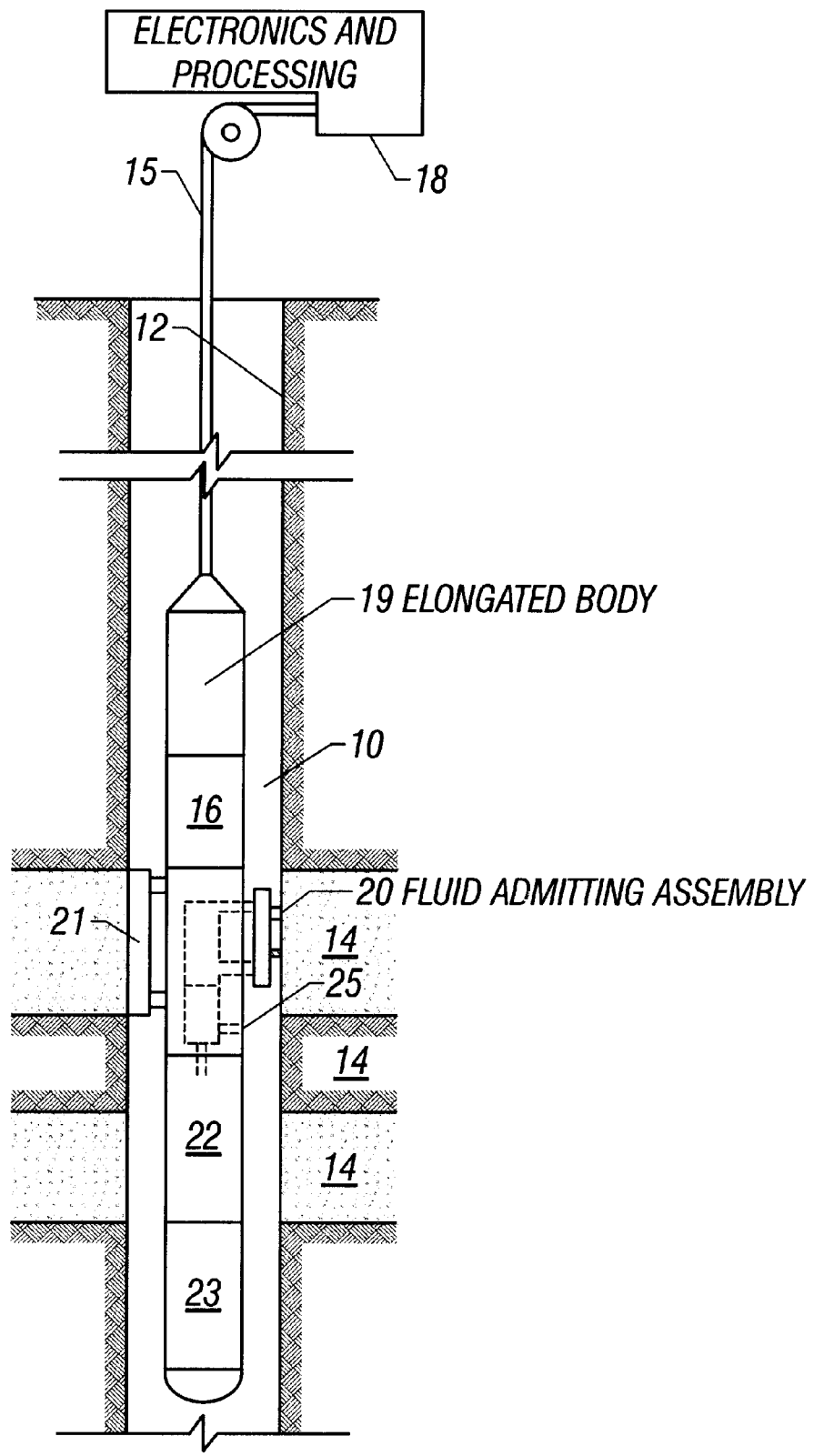
FIG. 1 is a schematic diagram of a borehole apparatus for analyzing formation fluids.

The instant invention is particularly applicable to both production logging and to borehole investigative logging. For purposes of brevity, however, the description herein will be primarily directed to borehole investigative logging, and the terms "borehole" and "borehole tool" should be read throughout the specification and claims to encompass a (cased) well and a tool used in a well, as well as in a borehole. Thus, a borehole tool 10 for testing earth formations and analyzing the compositions of fluids from the formation 14 in accord with the invention is seen in FIG. 1. As illustrated the tool 10 is suspended in the borehole 12 from the lower end of a typical multiconductor cable 15 that is spooled in a usual fashion on a suitable winch (not shown)

on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky, U.S. Pat. No. 3,813,936 to Urbanosky, and 3,811,321 to Urbanosky, as well as U.S. Pat. Nos. 4,860,581 and 4,936,139 to Zimmerman et al., which are hereby incorporated by reference herein. It should be appreciated, however, that it is not intended that the invention be limited to any particular method or apparatus for obtaining the formation fluids.

Figure 2:
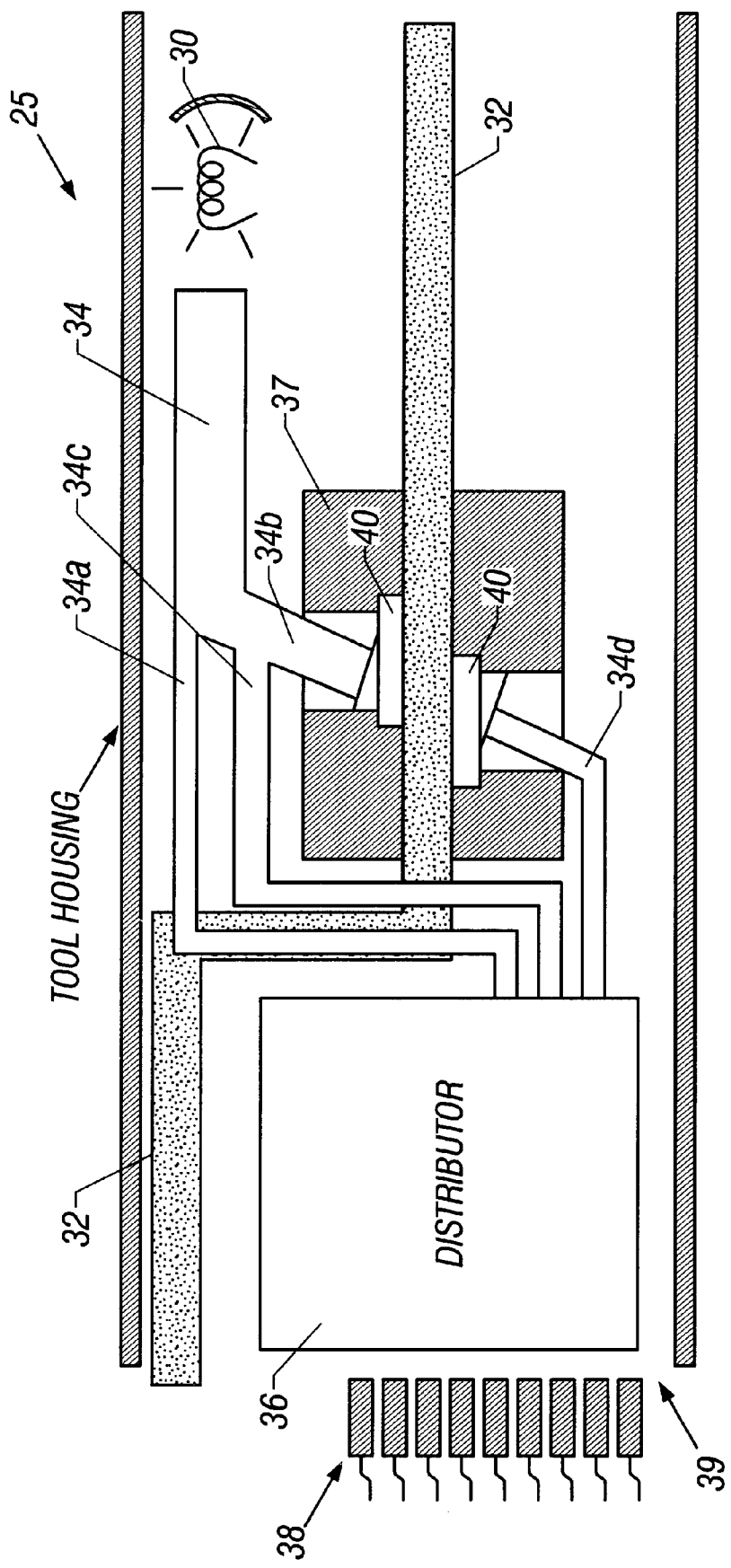
FIG. 2 is a schematic diagram of the optical system of the preferred near infrared fluid analysis module of FIG. 1.

Turning now to FIG. 2, a preferred fluid analysis module 25 includes a light source 30, a fluid sample tube 32 (coupled to the fluid admitting assembly 20 of FIG. 1), optical fibers 34, and a filter spectrograph 39 which includes a fiber coupler or distributor 36 and an associated detector array 38. The light source 30 is preferably an incandescent tungsten-halogen lamp which is kept at near atmospheric pressure. The light source 30 is relatively bright throughout the near infrared wavelength region of 1 to 2.5 microns and down to approximately 0.5 microns, and has acceptable emissions from 0.35 to 0.5 microns. Light rays from the light source 30 are preferably transported from the source to the fluid sample by at least part of a fiber optic bundle 34. The fiber optic bundle 34 is preferably split into various sections. A first small section 34a goes directly from the light source 30 to the distributor 36 and is used to sample the light source. A second section 34b is directed into an optical cell 37 through which the sample tube 32 runs and is used to illuminate the fluid sample. A third bundle 34d collects light transmitted or scattered through the fluid sample and provides the filter spectrograph with the light for determining the absorption spectrum of the fluid sample. Optionally, though not necessarily preferred, a fourth fiber optic bundle 34c collects light substantially backscattered from the sample for spectrographic analysis. The backscattered spectrum may be useful if multiple phases are present simultaneously. A three position solenoid (not shown) is used to select which fiber optic bundle is directed toward the filter spectrograph 39. Preferably, a light chopper (not shown) modulates the light directed at the spectrograph at 500 Hz to avoid low frequency noise in the detectors.

As mentioned above, optical bundle 34b directs the light towards the fluid sample. The fluid sample is obtained from the formation by the fluid admitting assembly 20 and is sent to the fluid analysis section 25 in tube 32. The sample tube 32 is preferably a two by six millimeter rectangular channel which includes a section 40 with windows made of sapphire. This window section 40 is located in the optical cell 37 where the light rays are arranged to illuminate the sample. Sapphire is chosen for the windows because it is substantially transparent to the spectrum of the preferred light source and because it is highly resistant to abrasion. As indicated schematically in FIG. 2, the window areas 40 may be relatively thick compared to the rest of the tube 32 to withstand high internal pressure. The fiber optic bundles 34b and 34d are preferably not perpendicular to the window areas 40 so as to avoid specular reflection. The window areas are slightly offset as shown in FIG. 2 to keep them centered in the path of the transmitted light. The signals from the detectors are digitized, multiplexed, and transmitted uphole via the cable 15 to the processing electronics 18 shown in FIG. 1.

Those skilled in the art will appreciate that each element in the detector array 38 is provided with a band pass filter for a particular wavelength band. According to a presently preferred embodiment, the MDT tool of Schlumberger is used to practice the invention. The MDT tool has a detector array of ten elements which detect light at or about the following wavenumbers:

21000 $cm^{-1}$, 18600 $cm^{-1}$, 15450 $cm^{-1}$, 9350 $cm^{-1}$, 7750 $cm^{-1}$, 6920 $cm^{-1}$, 6250 $cm^{-1}$, 6000 $cm^{-1}$, 5800 $cm^{-1}$, and 5180 $cm^{-1}$. It will be appreciated that the first three wavenumbers represent visible blue, green, and red light; these channels and adjacent NIR channels are preferably used to perform the type of analysis described in previously incorporated U.S. Pat. No. 5,266,800. The remaining wavenumbers are in the NIR spectrum and are used to perform various analyses described in other of the previously incorporated references.

As previously indicated, the detector array elements determine the intensity of the light passing through the fluid in the tube 32 at the ten different wavebands. For purposes of the present invention, however, it is only necessary that there be a single detector which detects NIR light around wavenumber 5800 $cm^{-1}$ or around wavenumber 6000 $cm^{-1}$. Preferably, however, at least two detectors, one each for 5800 $cm^{-1}$ and 6000 $cm^{-1}$ are utilized. Preferably, one or two detectors are also provided which measure a baseline intensity, in other words the intensity of a wavelength of light which is not absorbed by formation fluid, for example the detector at 9350 $cm^{-1}$ which is not absorbed by any formation fluid or 6920 $cm^{-1}$ which is not absorbed by hydrocarbons but is absorbed by water. The optical density of the fluid at particular wavelengths is determined according to Equation (1).

$$OD(\lambda) = \log \frac{I(\text{source})}{I(\lambda)} \quad (2)$$

where $I(\lambda)$ is the measured intensity at wavelength $\lambda$, and I (source) is the source intensity at the same wavelength. Thus, if the intensity at wavelength $\lambda$ is equal to the intensity of the source, there is no absorption, and the fraction in Equation (1) will be equal to 1 while the $OD(\lambda)$ will equal 0. If the intensity at wavelength $\lambda$ is one tenth the intensity of the source, the fraction in Equation (1) will be equal to 10 and the $OD(\lambda)$ will equal 1. It will be appreciated that as the intensity at $\lambda$ decreases, the optical density $OD(\lambda)$ will increase.

As mentioned above, the intensity of the source is preferably measured by measuring the light passing through the sample at a wavelength where no absorption occurs. This compensates for any light loss due to backscattering and provides a more accurate measure of optical density.

Figure 3:
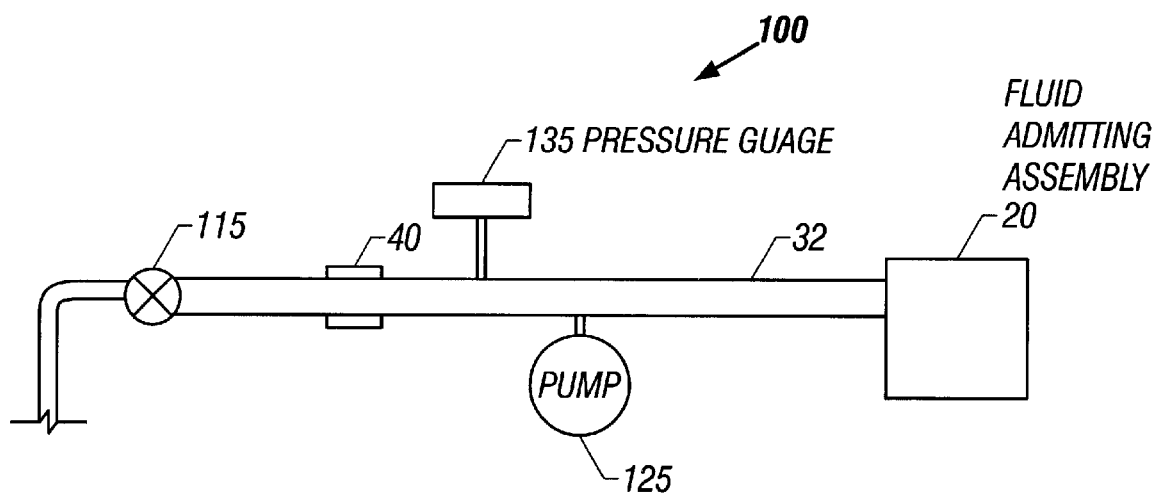
FIG. 3 is a schematic diagram of a fluid/electronic control system, for the near infrared fluid analysis module of FIG. 1.
Figure 4:
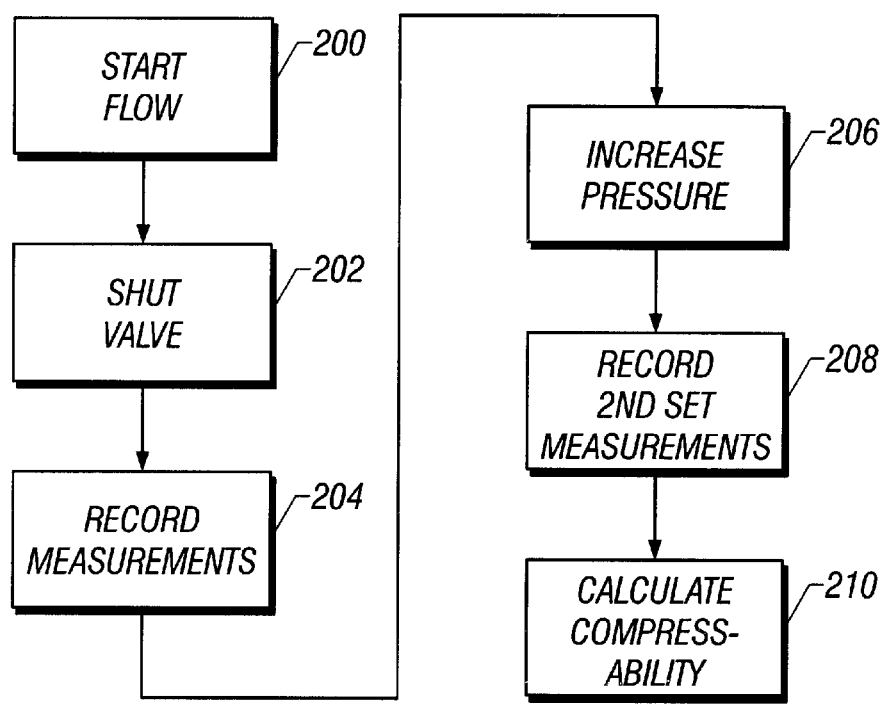
FIG. 4 is a flow-chart of the microprocessor control of the fluid/electronic control system of FIG. 3.

Turning now to FIG. 3, a schematic of the fluid/electronic control system 100 of the near infrared fluid analysis module 25 of FIG. 1 is shown. The fluid/electronic control system 100 preferably includes the fluid admitting assembly 20, the flow line 32, at least one valve 115 (for example, an isolation valve), a pump 125 (which may be part of a pump-out module, if desired), and a pressure gauge 135, all preferably electronically coupled to a microprocessor (not shown) located in one of the electrical control systems 16 and 18. As suggested by FIG. 4, at 200, the fluid admitting assembly is directed by the microprocessor to permit fluid to flow into the admitting assembly 20 and through the flow line 32 which extends through the optical cell 37. According to the invention, at 202, the valve 115 is shut under control of the microprocessor. Optical measurements, including a determination of the absorption of light at one or more desired wavelengths, are then recorded at 204 with respect to the fluid in the optical cell, and the pressure of the fluid as determined by the pressure gauge 135 is also recorded. Then, at 206, the pump 125 is used to increase the pressure of the fluid in the optical cell 37. As will be discussed in more detail hereinafter, the pressure of the fluid is preferably increased by at least 2000 psi and preferably by approximately 4000 psi, and at 208 a second set of absorption measurements at the desired wavelengths are recorded, as is the pressure of the fluid as determined by the pressure gauge 135. The compressibility of the hydrocarbon fluid is then calculated at 210 based on the optical measurements (in other words, the spectral absorptions) at the two different pressures. Details as to how the compressibility is determined are discussed below with reference to FIGS. 5–7.

Figure 5:
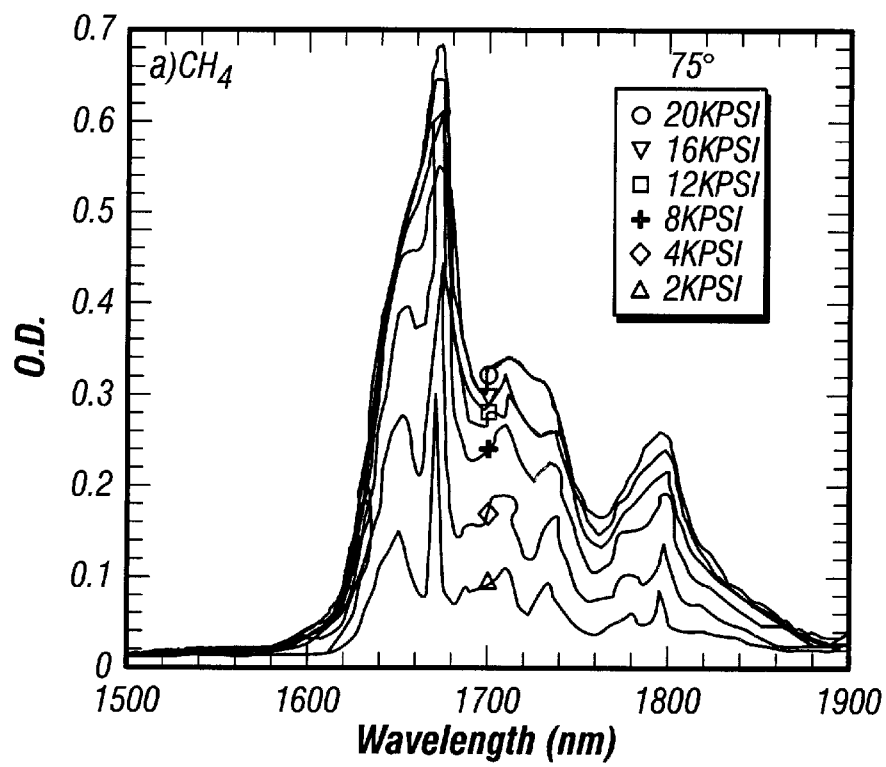
FIG. 5 is a graph plotting optical density versus wavelength for methane at various pressure conditions.

For a given hydrocarbon fluid, the magnitude of the absorption will depend upon the pressure of the fluid; the higher the pressure, the greater the absorption. According to the invention, it has been experimentally determined that the change in the absorption that results from a change in pressure correlates directly with fluid compressibility. FIG. 5 shows the change in the optical absorption spectrum which results from changes in pressure for pure methane gas. In particular, the absorption peak in the 1640–1675 nm range (in other words, the "methane absorption peak") is seen to increase from an optical density of approximately 0.3 to an optical density of nearly 0.7 as pressure is increased from 2 kpsi to 20 kpsi.

Figure 6:
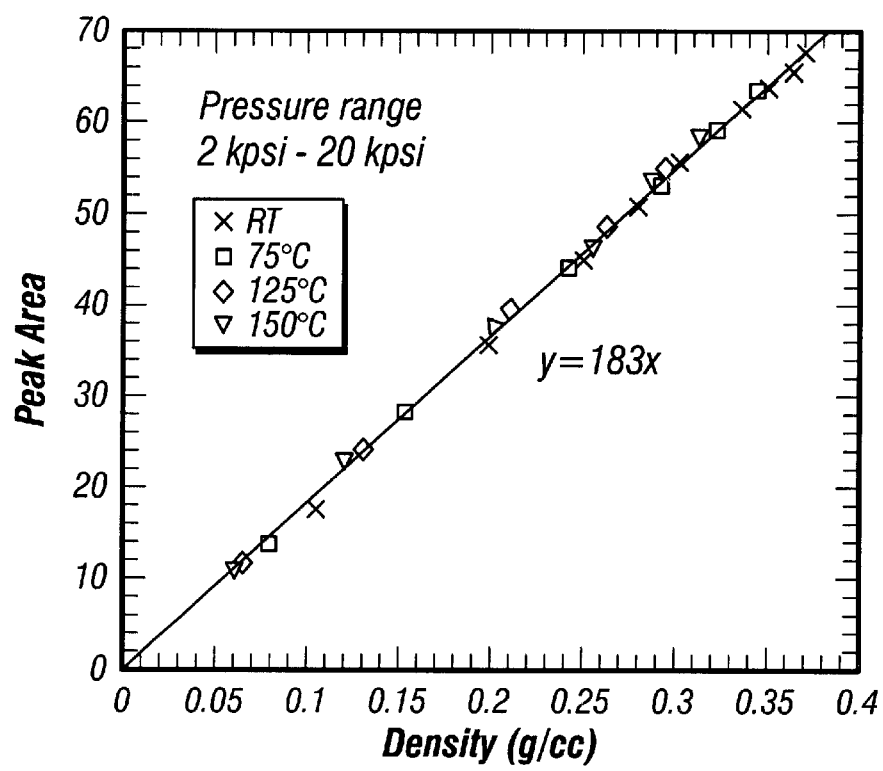
FIG. 6 is a graph plotting optical density peak area for methane versus density at various wavelengths of interest.
Figure 7:
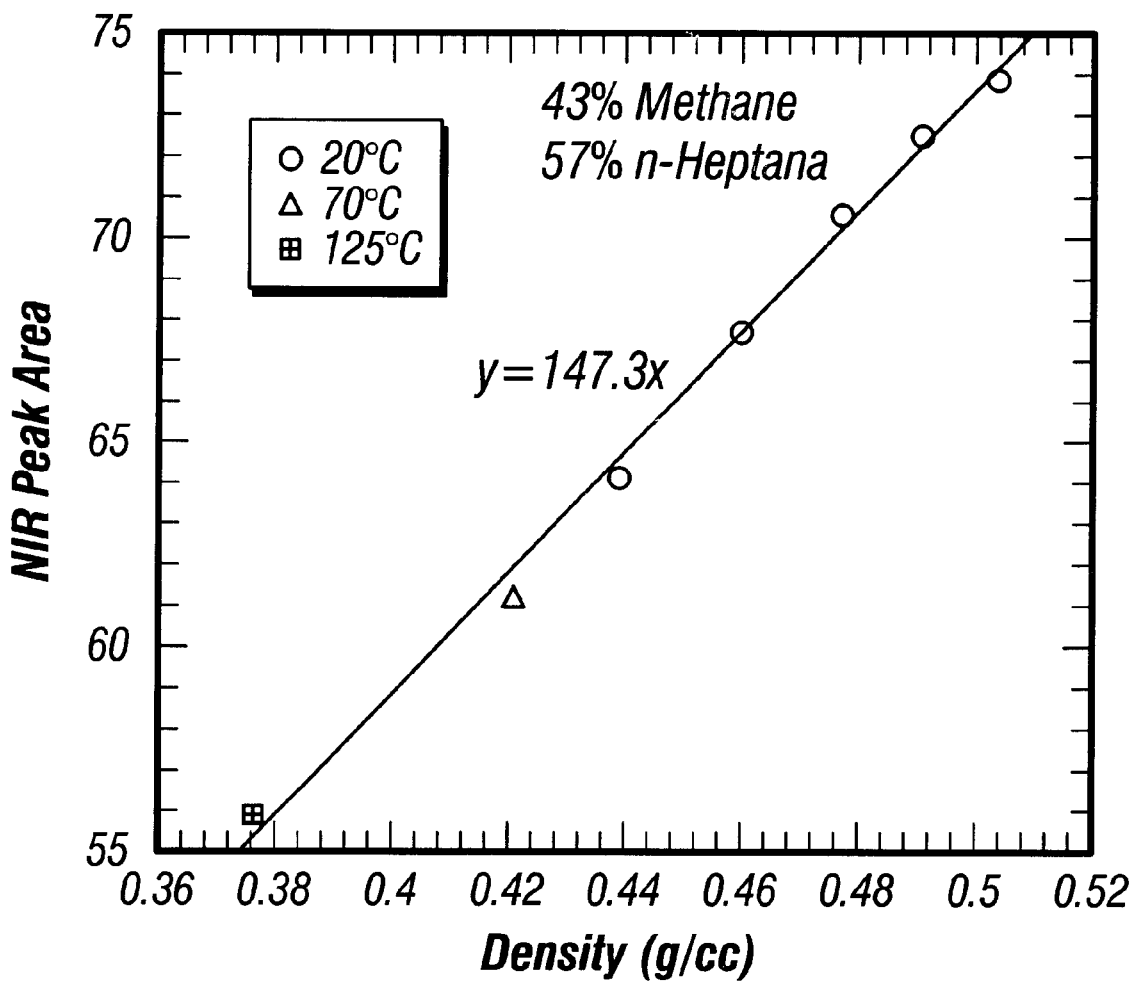
FIG. 7 is a graph plotting optical density peak area versus density for a methane/heptane hydrocarbon mixture.

By integrating the area under each of the curves of FIG. 5, "peak areas" (in other words, the area under the optical density peak) can be found. As seen in FIG. 6, the optically determined peak areas of methane at different temperatures have a linear relationship with the mass density of the methane at those temperatures. Likewise, as seen in FIG. 7, the optically determined peak areas of a methane/heptane hydrocarbon mixture have a linear relationship with the mass density of the mixture at different temperatures. By comparing FIG. 7 with FIG. 6, it will be appreciated that the slope of the line defining the linear relationship between peak areas and mass density is specific to the hydrocarbon fluid or fluid mixture being analyzed.

Given the above, a relative change in fluid volume (due to a change in pressure) can be related to a change in density according to $$\partial V/V = -\rho/\rho, \quad (3)$$

where V is the volume and $\rho$ is the density of the fluid. Since there is a linear relationship between the density $\rho$ and the peak area $\Psi$; in other words, $\Psi = m\rho$, where m is a constant, it follows that $$\partial \Psi = m\partial \rho/\rho \quad (4)$$

Therefore, using equations (1), (3) and (4), $$\beta = \frac{1}{\Psi}\left(\frac{\partial \Psi}{\partial P}\right)_T \quad (5)$$

where $\beta$ is the fluid compressibility, $\partial \Psi$ is the difference in peak areas, $\partial P$ is the difference in pressure, and the peak area $\Psi$ is a variable which changes as the pressure changes. It is noted that equation (5) can be estimated according to:

$$\beta = \frac{1}{\Psi}\left(\frac{\Delta \Psi}{\Delta P}\right)_T \quad (6)$$

where $\Psi$ is preferably the initial peak area, and $\Delta\Psi = \partial\Psi$ and $\Delta P = \partial P$. From equations (5) and (6), it is evident that at any given temperature, fluid compressibility can be determined from the change in the peak area (due to the change in pressure) divided by the change in pressure, and the peak area itself. According to the invention, the change in pressure is measured by the pressure gauge 135, while the change in peak area is measured by the optical sensors. It is noted that the peak area determination for a particular sensor is determined from the raw data count of the sensor (I ($\lambda$)) and equation (2); in other words, the peak area is the optical density for the wavelength width of that channel. Thus, according to the preferred embodiment of the invention, optical sensors at wavelengths corresponding to peak areas of hydrocarbon fluids which are likely to be encountered in the formation are utilized; for example, at and/or around 6,000 cm$^{-1}$ and 5,800 cm$^{-1}$ (the absorption peaks of methane and crude oil respectively).

Therefore, methods according to the invention include providing an OFA-type tool which subjects formation fluids to NIR illumination and which provides a spectral absorption measurement of peaks at and/or around about 6,000 cm$^{-1}$ and about 5,800 cm$^{-1}$ (the absorption peaks of methane and crude oil respectively), measuring the spectral absorptions at two different pressures, and determining the compressibility of the fluid from the change in the peak areas, the change in pressure, and the peak area itself.

Because the determination of compressibility relies upon a measurement of the change in peak area, the change in pressure must be chosen to result in an observable difference in peak areas. Using equation (6) above, if a typical compressibility for a hydrocarbon at a high pressure is approximately 5×10$^{-6}$ psi$^{-1}$, and a typical value for the peak area equal to 0.6 OD for a narrow bandwidth channel (as seen in FIG. 5), in order to obtain a one percent change in peak area (in other words, 0.006 OD), the pressure must be increased by approximately 2000 psi. Therefore, according to the preferred embodiment of the invention, the pressure increase is chosen to be at least 2000 psi, and more preferably at least 4000 psi.

Returning now to FIGS. 3 and 4, it will be appreciated that different equipment and different methods can be utilized in order to obtain the desired optical measurements at different pressures. For example, rather than first closing a valve and then taking a first optical measurement, assuming that the fluid flowing through the optical cell is substantially uniform over a short period of time, the first optical measurement can be taken before closing the valve. Also, rather than using a single valve, multiple valves can be utilized. Further, it should be appreciated that pumps, valves, and other equipment already available on a tool such as the OFA can be controlled to implement the invention; or that alternatively, dedicated equipment can be added to a tool such as the OFA, or utilized in a tool especially design for purposes of the invention in order to implement the invention.

There have been described and illustrated herein methods and apparatus for optically measuring fluid compressibility downhole. While particular embodiments of the invention have been described, it is not intended that the invention be limited thereto, as it is intended that the invention be as broad in scope as the art will allow and that the specification be read likewise. Thus, while the invention has been described with respect to a particular commercial tool (the OFA of Schlumberger), it will be appreciated that the invention may be practiced utilizing other equipment. Also, while particular optical equipment has been described, it will be appreciated that other equipment can be used as well provided that an indication of peak areas and changes in peak areas due to a change in pressure can be measured. Thus, for example, different light sources can be utilized provided the source provides NIR waves at the wavelengths of interest. Likewise, although fiber optics are preferred, different means for directing light to the optical cell can be utilized; and different means for gathering and analyzing the amount of light which traverses the cell can also be utilized. Similarly, while particular equipment relating to obtaining and pressurizing fluid samples has been described, it will be appreciated that other equipment can be used to obtain the fluid samples and to pressurize the samples. In addition, while the invention was described with reference to increasing the pressure on the sample, it will be appreciated that the pressure can be decreased, as long as a suitable difference in pressure is obtained. If the pressure is decreased, care should be taken to avoid reaching the bubble point of the fluid; in other words, so that gas does not evolve in the optical cell. It will therefore be appreciated by those skilled in the art that yet other modifications could be made to the provided invention without deviating from its spirit and scope as claimed.

We claim:

1. A borehole apparatus for measuring downhole the compressibility of hydrocarbon fluid in a formation, comprising:
   a) a testing region;
   b) a conduit for directing the formation fluid into said testing region;
   c) means for measuring pressure on the fluid in said testing region;
   d) means for changing pressure on the fluid in said testing region;
   e) a light source which emits at least near infrared rays into said testing region;
   f) a spectral detector optically coupled to said testing region; and
   g) a processing means coupled to said spectral detector and to said means for measuring pressure, said processing means for determining said compressibility of said hydrocarbon fluid as a function of a change in pressure determined from at least two measurements made by said means for measuring pressure and as a function of measurements made by said spectral detector.

2. A borehole apparatus according to claim 1, wherein:
said testing region is a transparent tube or chamber through which the hydrocarbon fluid flows and which is located between said light source and said spectral detector.

3. A borehole apparatus according to claim 1, wherein:
said spectral detector comprises means for measuring the intensity of light at at least one wavelength which has been transmitted through the fluid in said testing region.

4. A borehole apparatus according to claim 3, wherein:
said at least one wavelength comprises a plurality of wavelengths.

5. A borehole apparatus according to claim 3, wherein:
said at least one wavelength comprises approximately 1660 nanometers.

6. A borehole apparatus according to claim 1, wherein:
said spectral detector comprises means for measuring the intensity of light at at least one wavelength range which has been transmitted through the fluid in said testing region.

7. A borehole apparatus according to claim 6, wherein:
said at least one wavelength range comprises a range from approximately 1640 nm to approximately 1675 nm.

8. A borehole apparatus according to claim 1, wherein:
said change of pressure comprises a change of at least 2000 pounds per square inch (psi).

9. A borehole apparatus according to claim 3, wherein:
said processing means determines compressibility according to $$\beta = \frac{-1}{\Psi}\left(\frac{\Delta\Psi}{\Delta P}\right)_T \text{ or } \beta = \frac{1}{\Psi}\left(\frac{\partial\Psi}{\partial P}\right)_T$$

where $\beta$ is said compressibility of said fluid, $\Psi$ is a peak area at said at least one wavelength, $\Delta P$ and $\partial P$ are said change in pressure, $\Delta\Psi$ and $\partial\Psi$ are a change in peak area, and T is a temperature.

10. A borehole apparatus according to claim 9, wherein:.
said peak area is determined as a function of a known emission of said light source and of said measurements made by said spectral detector.

11. A borehole apparatus according to claim 1, wherein:
said means for changing pressure comprises at least one valve and a pump coupled to said conduit.

12. A method for determining the compressibility of hydrocarbon fluid in a formation, comprising:
   a) obtaining a sample of said hydrocarbon fluid from said formation;
   b) conducting a first spectral analysis of said sample at a first pressure to obtain first spectral results;
   c) exposing said sample or an equivalent sample of hydrocarbon fluid to a second pressure different than said first pressure;
   d) conducting a second spectral analysis of said sample or said equivalent sample at said second pressure to obtain second spectral results;
   e) determining an indication of said compressibility of said hydrocarbon fluid from an indication of said first pressure, an indication of said second pressure, and said first and second spectral results.

13. A method according to claim 12, wherein:
said second pressure differs from said first pressure by at least 2000 pounds per square inch (psi).

14. A method according to claim 12, wherein:
said first spectral analysis comprises detecting an intensity of light transmitted through the sample at at least one near infrared wavelength, and said second spectral analysis comprises detecting a second intensity of light transmitted through the sample at said at least one near infrared wavelength.

15. A method according to claim 14, wherein:
said at least one near infrared wavelength comprises a plurality of near infrared wavelengths.

16. A method according to claim 14, wherein:
said at least one near infrared wavelength comprises approximately 1660 nanometers.

17. A method according to claim 12, wherein:
said first spectral analysis comprises detecting an intensity of light transmitted through the sample at at least one near infrared wavelength range, and said second spectral analysis comprises detecting a second intensity of light transmitted through the sample at said at least one near infrared wavelength range.

18. A method according to claim 17, wherein:
said at least one near infrared wavelength range comprises a range from approximately 1640 nm to approximately 1675 nm.

19. A method according to claim 14, wherein:
said indication of compressibility is determined according to $$\beta = \frac{-1}{\Psi}\left(\frac{\Delta\Psi}{\Delta P}\right)_T \text{ or } \beta = \frac{1}{\Psi}\left(\frac{\partial\Psi}{\partial P}\right)_T$$

where $\beta$ is said compressibility of said fluid, $\Psi$ is a peak area at said at least one wavelength, $\Delta P$ and $\partial P$ are said change in pressure, $\Delta\Psi$ and $\partial\Psi$ are a change in peak area, and T is a temperature.

20. A method according to claim 12, wherein:
said first pressure and said second pressure are above a bubble point pressure of said sample.

21. A borehole apparatus for measuring downhole the compressibility of hydrocarbon fluid in a formation, comprising:
   a) a testing region;
   b) a conduit for directing the formation fluid into said testing region;
   c) a sensor for measuring pressure on the fluid in said testing region;
   d) means for changing pressure on the fluid in said testing region;
   e) a light source which emits at least near infrared rays into said testing region;
   f) a spectral detector optically coupled to said testing region; and
   g) a processor coupled to said spectral detector and to said sensor, said processor for determining the compressibility of the formation fluid as a function of a change in pressure determined from at least two pressure measurements made by said sensor and as a function of measurements made by said spectral detector.

* * * * *